(12) United States Patent
Swenson et al.

(10) Patent No.: US 7,304,298 B2
(45) Date of Patent: Dec. 4, 2007

(54) PHOTOEMISSIVE ION MOBILITY SPECTROMETRY IN AMBIENT AIR

(75) Inventors: Orven F. Swenson, Fargo, ND (US); Feng Hong, Potsdam, NY (US)

(73) Assignee: North Dakota State University, Fargo, ND (US)

(*) Notice: Subject to any disclaimer, the term of this patent is extended or adjusted under 35 U.S.C. 154(b) by 0 days.

(21) Appl. No.: 11/491,508

(22) Filed: Jul. 20, 2006

(65) Prior Publication Data

US 2007/0114395 A1    May 24, 2007

Related U.S. Application Data

(60) Provisional application No. 60/701,613, filed on Jul. 21, 2005.

(51) Int. Cl.
*H01J 49/40* (2006.01)
*H01J 49/16* (2006.01)

(52) U.S. Cl. ............... 250/287; 250/288; 250/423 P

(58) Field of Classification Search .......... 250/287, 250/288, 423 P

See application file for complete search history.

(56) References Cited

U.S. PATENT DOCUMENTS

| 3,514,658 A | * | 5/1970 | Davis et al. | ............. 313/535 |
| 3,902,064 A | * | 8/1975 | Young | ............. 250/287 |
| 4,837,441 A | * | 6/1989 | Hurrell | ............. 250/423 P |

* cited by examiner

*Primary Examiner*—Jack I. Berman
(74) *Attorney, Agent, or Firm*—John P. O'Banion

(57) ABSTRACT

A photoemissive ion mobility spectrometer is disclosed for of chlorinated hydrocarbons and nitro-organic materials. Backside illumination of a thin gold film by pulsed laser radiation, pulsed ultraviolet xenon flashlamp, or like UV source, is used to produce bursts of low energy photo-emitted electrons. These swarms of thermalized electrons are directly attached by electronegative analytes or by reactant molecules, followed by charge transfer to the more electronegative analyte. Total internal reflection is incorporated for the backside illumination using optical elements such as a fused silica prism. The spectrometer allows for the direct vaporization of adsorbed explosive molecules from surfaces followed by direct injection into the photoemissive ion mobility spectrometer through a heated inlet.

32 Claims, 11 Drawing Sheets

PHOTOEMISSIVE ION MOBILITY SPECTROMETRY IN AMBIENT AIR

CROSS-REFERENCE TO RELATED APPLICATIONS

This application claims priority from U.S. provisional application Ser. No. 60/701,613 filed on Jul. 21, 2005.

STATEMENT REGARDING FEDERALLY SPONSORED RESEARCH OR DEVELOPMENT

This invention was made with Government support under Grant No. EPS-0083063, awarded by the National Science Foundation Experimental Program to Stimulate Competitive Research, and Contract No. F08637-98-C6009 through Dakota Technologies, Inc., supported by the Air Force Research Laboratory and the Strategic Environmental Development Program (SERDP). The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to ion mobility spectrometers, and more particularly to photoemissive ion mobility spectrometers.

2. Description of Related Art

Ion mobility spectrometry (IMS) using a radioactive ionization source has become the standard method for the detection of trace quantities of explosives. Detection of chlorinated solvents, such as trichloroethylene and tetrachloroethylene, in the air and soil remains important for providing a safe environment. The advantages of IMS are its sensitivity in the ppb or pg range, its continuous real-time monitoring capability, its relatively low cost, and its portability due to instrumental simplicity.

Currently available commercial IMS instruments use radioactive sources that have significant deficiencies. Successful examples of nonradioactive sources for IMS using thermionic ionization, photoionization, laser ionization, corona discharge ionization, and electrospray ionization have been reported for a variety of applications.

Traditional IMS instruments employ β-particles (high-energy electrons) emitted from a $^{63}Ni$ radioactive source to ionize nitrogen, a dominant component of carrier gases. Before analyte is ionized and able to be detected, a very complex sequence of ion-molecule reactions and energy-loss collisions occurs that produces both positive and negative reactant ions including low-energy electrons. When trace analyte vapor exists in the carrier gas, ion-molecule reactions between reactant ions and analyte neutrals generate product ions characteristic of the analyte. In the drift region, the ions assume characteristic drift velocities in the applied electric field such that at the end of the drift region individual ion products arrive at a collector electrode in swarms. The swarms appear as peaks in an ion mobility spectrum, which is simply a plot of collector current as a function of time. Drift times of the peaks permit identification of the ion products.

The use of photoemitted electrons from thin metallic films exposed to ultraviolet light in an electron-capture detector (ECD), eliminating the need for the radioactive $^{63}Ni$ emitter, has been previously reported (Simmonds, P. G. *Journal of Chromatography* 1987, 399, 149-64). In air, the photoemitted electrons start with a maximum energy of only 0.4 eV and very rapidly acquire a mean electronic energy at 293 K equal or close to 3/2 kT (0.037 eV). Consequently, no positive ions or energized radicals are produced. Elimination of the positive ions prevents a large electron-positive ion recombination in the reaction region. The chemical processes within the detection cell are simplified considerably if positive ions are absent thus making interpretation of the measured signal more straightforward.

Begley et al. demonstrated the detection of trace analyte vapor in air using an ion mobility spectrometer fitted with a photoemissive ionization source (PE-IMS). They (Begley et al., *Journal of Chromatography* 1991, 588, 239-49) found that where oxygen is present, the ion mobility resolution is effectively unchanged at oxygen concentrations in excess of 6% and decreases as the oxygen content is decreased due to free electrons traveling further distances before being attached to oxygen. The Begley device was demonstrated for acetylacetone, benzoylacetone and benzoquinine. The Begley et al. device, however, used normal incidence illumination of the ionization source resulting in transmission of U.V. light into the ionization chamber, which lowers the free electron count and sensitivity and makes photochemical reactions in the ionization chamber likely.

Because detection of electronegative compounds such as chlorocarbons and nitro-organics require only low-energy electron attachment, electron photoemission (PE) is an advantageous alternative ionization source. The low-energy electrons generated are unable to ionize gas molecules by impact, which would produce both positive and negative ions. Instead, electronegative components of the carrier gas, including analyte if present, attach electrons with no loss due to recombination of positive and negative ions. Another advantage is that the number of electrons generated increases with the intensity of the incident light, permitting the number of electrons to be tailored to a particular analysis. Due in part to these advantages, photoemissive sources have appeared frequently throughout the past century in experimentation requiring low-energy electrons, including both the ECD and extensive implementation in instruments for physical studies of electron interactions with gas molecules.

Therefore an object of the present invention is a photoemissive ion mobility spectrometer with improved sensitivity for detection for compounds such as chlorocarbons and nitro-organics.

BRIEF SUMMARY OF THE INVENTION

The present invention is directed to photoemissive ion mobility spectrometry of chlorinated hydrocarbons and nitro-organic materials. Backside illumination of a thin gold film by pulsed laser radiation, pulsed ultraviolet xenon flashlamp, or like UV source, is used to produce bursts of low energy photo-emitted electrons. These swarms of thermalized electrons are directly attached by electronegative analytes or by reactant molecules, followed by charge transfer to the more electronegative analyte.

Total internal reflection is incorporated for the backside illumination using optical elements such as a fused silica prism. This enhances the photo-emitted current by at least a factor of five and avoids photochemistry of the analytes by preventing the ultraviolet light from entering the gas flow region. A significant enhancement in the nitro-organic signal was observed using air as the carrier gas. The spectrometer of the present invention allows for the direct vaporization of adsorbed explosive molecules from surfaces followed by direct injection into the photoemissive ion mobility spectrometer through a heated inlet.

The photoemissive approach of the present invention creates the anions in the plane of a thin film metal coating in very large numbers without the electronic shutter grid losses. The shutter grid pulse width is one of the factors determining the resolution of a conventional linear IMS. Typical IMS shutter pulse widths are 50-500 µs. Because the photoemissive technique is expected to produce reactant ion pulse widths on the order of 20 µs, higher resolution than the conventional IMS is achievable.

The present invention demonstrates successful IMS detection of chlorinated solvents and nitro-organic species (i.e., explosives) in ambient air using an alternative photoemissive ionization via electron attachment.

An aspect of the invention is a photo-emissive ion mobility spectrometer for the detection of electron-attaching vapors. The spectrometer comprises a photoemissive ionization source configured to generate free electrons and respective ions, and a drift tube having an axis and a first end disposed adjacent the photoemissive ionization source. The drift tube is configured to separate the ions before reaching a collecting electrode disposed opposite the photoemissive ionization source at a second end of said drift tube. An aperture grid is disposed in front of the collecting electrode such that the collecting electrode is configured to detect presence of the ions located between the aperture grid and the collecting electrode.

Another aspect is a method for detecting electron-attaching vapors in an airspace, comprising directing a light source at an optical element having a thin film coating at one end, generating free electrons and respective ions as a result of the light source impinging on the thin film coating, and separating the ions along an axis of a drift tube having a free end disposed adjacent the prism, and detecting presence of the ions on a second end of the drift tube opposite the optical element.

Another aspect is a photoemissive ion mobility spectrometer for the detection of an analyte. The spectrometer comprises an ionization chamber configured to receive analyte, e.g. chlorinated solvents and nitro-organic species collected from a sample surface. A photoemissive ionization source is disposed at a first end of the ionization chamber. The photoemissive ionization source comprises an optical element having a back surface disposed adjacent the ionization chamber. The optical element is configured to receive a beam of light from a location external to the ionization chamber and direct the beam at the back surface. The back surface of optical element is configured to illuminate under total internal reflection of the beam such that the beam does not enter the ionization chamber. The backside illumination of the optical element generates ions (characteristic of the received analyte) in the chamber.

In one embodiment of the current aspect, a detector is disposed at a second end of the ionization chamber opposite the photoemissive ionization source. The detector is configured to detect presence of said ions generated by the photoemissive ionization source. A drift tube is preferably disposed between the photoemissive ionization source and the detector to generate an electric field to separate said ions and direct the ions from the photoemissive ionization source to the detector.

Generally, the back surface of the optical element comprises a thin metal coating, such as gold, aluminum, silver etc.

In a preferred embodiment, the optical element comprises a prism that is configured to direct the beam at the metal coating at an angle of incidence beyond a critical angle of the prism.

Alternatively, the optical element may be configured to generate multiple internal reflections on the back surface of the optical element, e.g. a waveguide or bare core of a fiber optic.

The ionization source preferably comprises an UV light source configured to direct the beam of light at the optical element, such as a laser or flash lamp. Alternatively, the ionization source may comprise a plurality of individual optical elements (e.g. LED's), wherein each of the individual optical elements directs a beam of light at one of the individual optical elements.

In another embodiment, the spectrometer comprises an inlet tube coupled to the ionization chamber, wherein the inlet tube is configured to direct the analyte under ambient air into the ionization chamber. The inlet tube may be heated to vaporize the analyte from a sample surface for collection.

Another aspect of the invention is a method for detecting an analyte, comprising directing a beam of light at an optical element having a coating at one end. The beam of light is configured to illuminate the coating to produce photoemission, and is reflected off of said coating under total internal reflection. Ions are generated as a result of the beam of light illuminating the coating the presence of the ions is detected opposite the optical element.

The method may further comprise separating the ions along an axis of a drift tube having a free end disposed adjacent the optical element, and detecting the presence of the ions on a second end of the drift tube opposite the optical element. The reduced ion mobilities of the ions generated in the drift tube are then measured.

Separating the ions generally comprises directing a counter-flowing drift gas through a plurality of rings and an aperture grid that generate a uniform electric field along an axis of the drift tube. The plurality of rings may be separated by resistors, such that a voltage is supplied to the rings to generate the electric field.

In a preferred embodiment, the carrier gas comprises ambient air. The ambient air may also be heated prior to entering the drift tube. For example, adsorbed analytes from a sample surface may be directly injected into the drift tube through a heated inlet.

Another aspect is photoemissive ion mobility spectrometer comprising an ionization chamber configured to receive an analyte, a photoemissive ionization source disposed at a first end of the ionization chamber. The photoemissive ionization source comprises an optical element having a back surface disposed adjacent the ionization chamber such that it forms at least a portion of an internal wall of the ionization chamber. The optical element is configured to receive a beam of light from a location external to the ionization chamber and direct the beam at the back surface, such that the back surface illuminates under total internal reflection of the beam and the beam reflects external the ionization chamber. A detector is disposed at a second end of the ionization chamber opposite the photoemissive ionization source. A drift tube is disposed between the photoemissive ionization source and the detector. The backside illumination of the optical element generates ions characteristic of the received analyte in the chamber. The drift tube is configured to generate an electric field to separate the ions and direct the ions from the photoemissive ionization source to the detector, which is configured to detect presence of the ions generated by the photoemissive ionization source.

Preferably, the back surface of the optical element is configured such that none of the beam enters the ionization chamber.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 11:
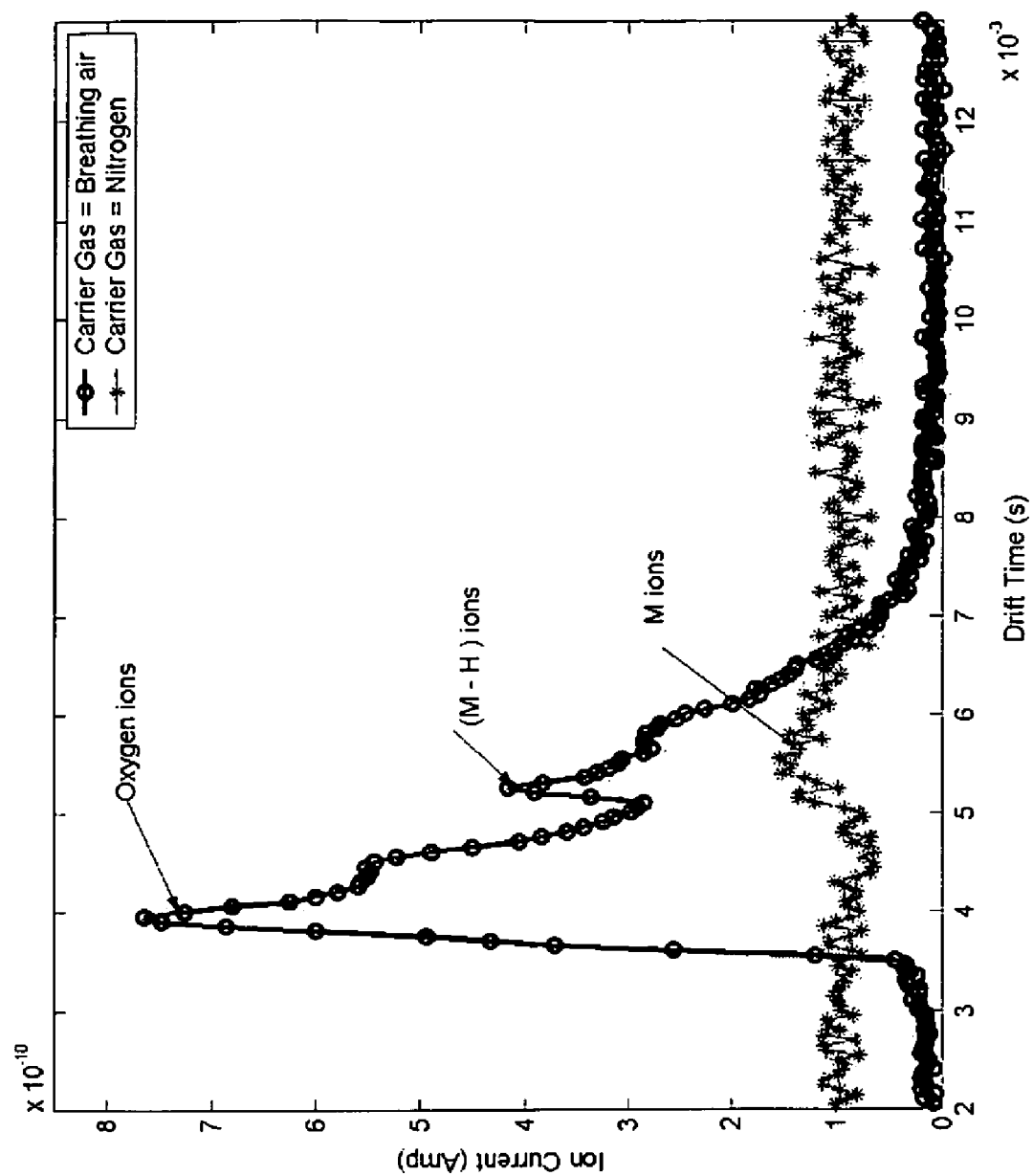
Figure 12:
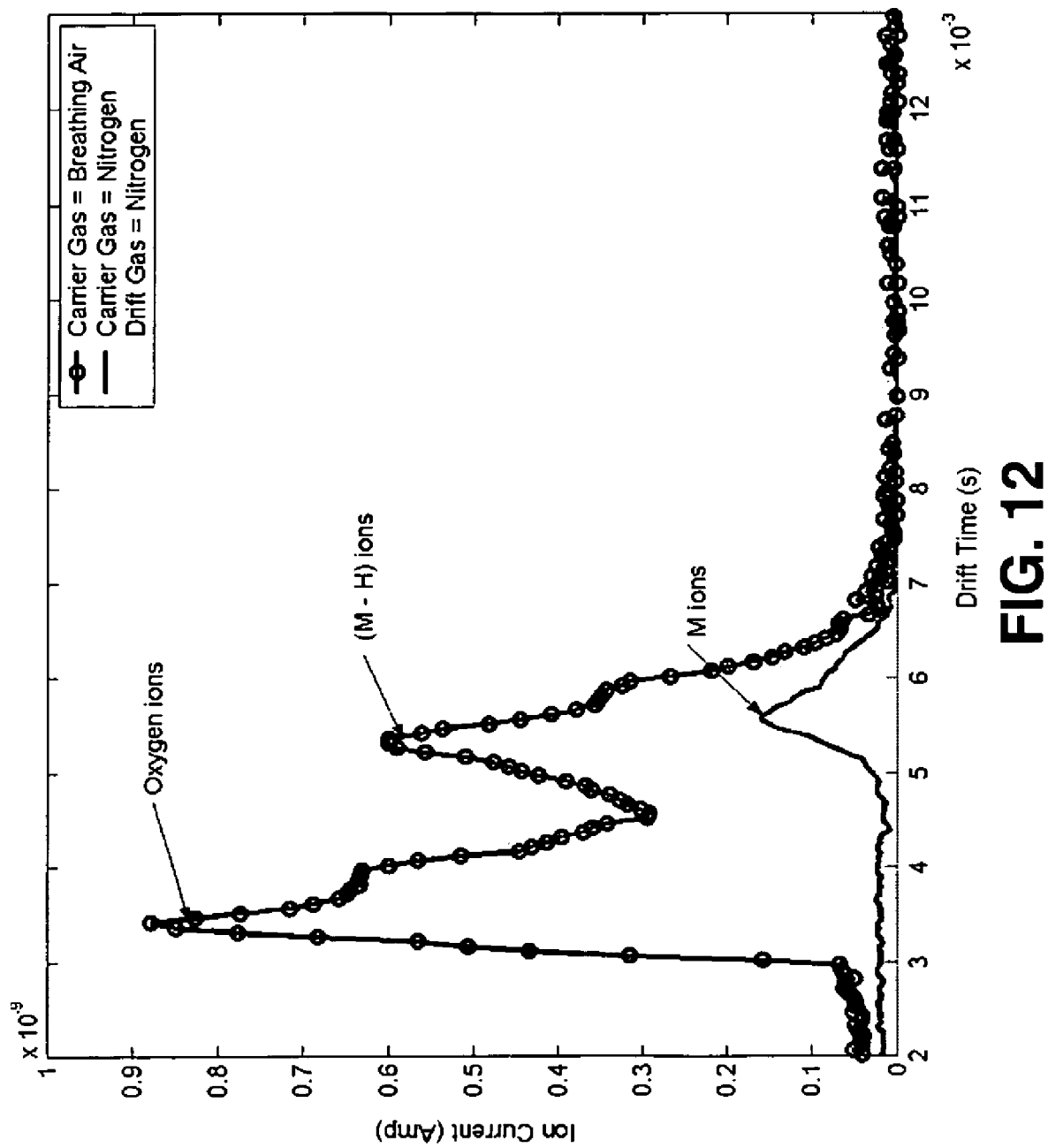
Figure 13:
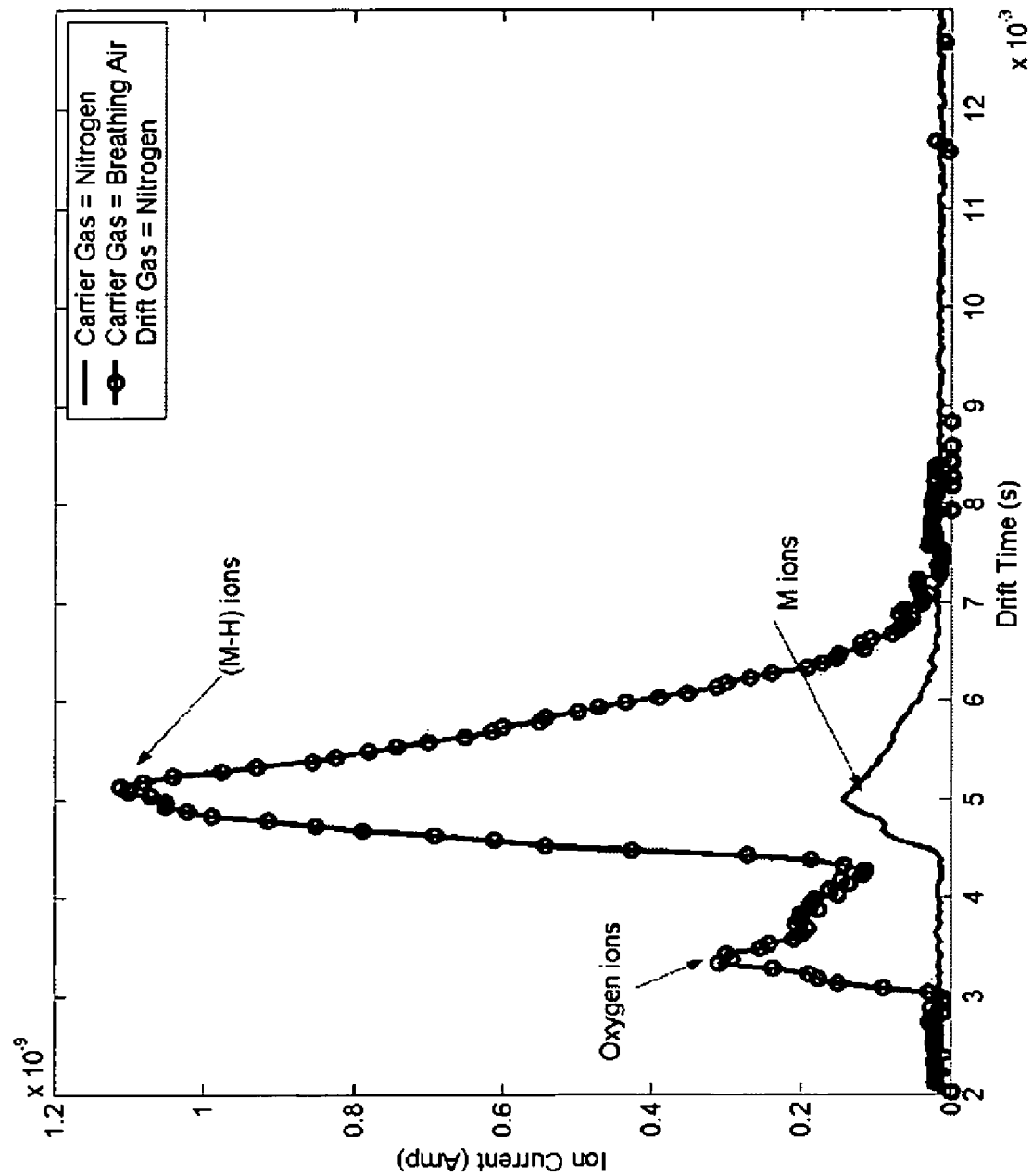

FIG. 11 shows a comparison of 2,4-dinitrotoluene ion mobility spectra between using the breathing-grade air and ultra pure nitrogen gas as carrier gases FIG. 12 shows a comparison of 2,6-dinitrotoluene ion mobility spectra between using breathing-grade air and ultra pure nitrogen gas as carrier gases FIG. 13 shows comparison of p-nitrotoluene ion mobility spectra between using breathing-grade air and ultra pure nitrogen gas as carrier gases

DETAILED DESCRIPTION OF THE INVENTION

Referring more specifically to the drawings, for illustrative purposes the present invention is embodied in the apparatus generally shown in FIG. 1 through FIG. 13. It will be appreciated that the apparatus may vary as to configuration and as to details of the parts, and that the method may vary as to the specific steps and sequence, without departing from the basic concepts as disclosed herein.

Figure 1:
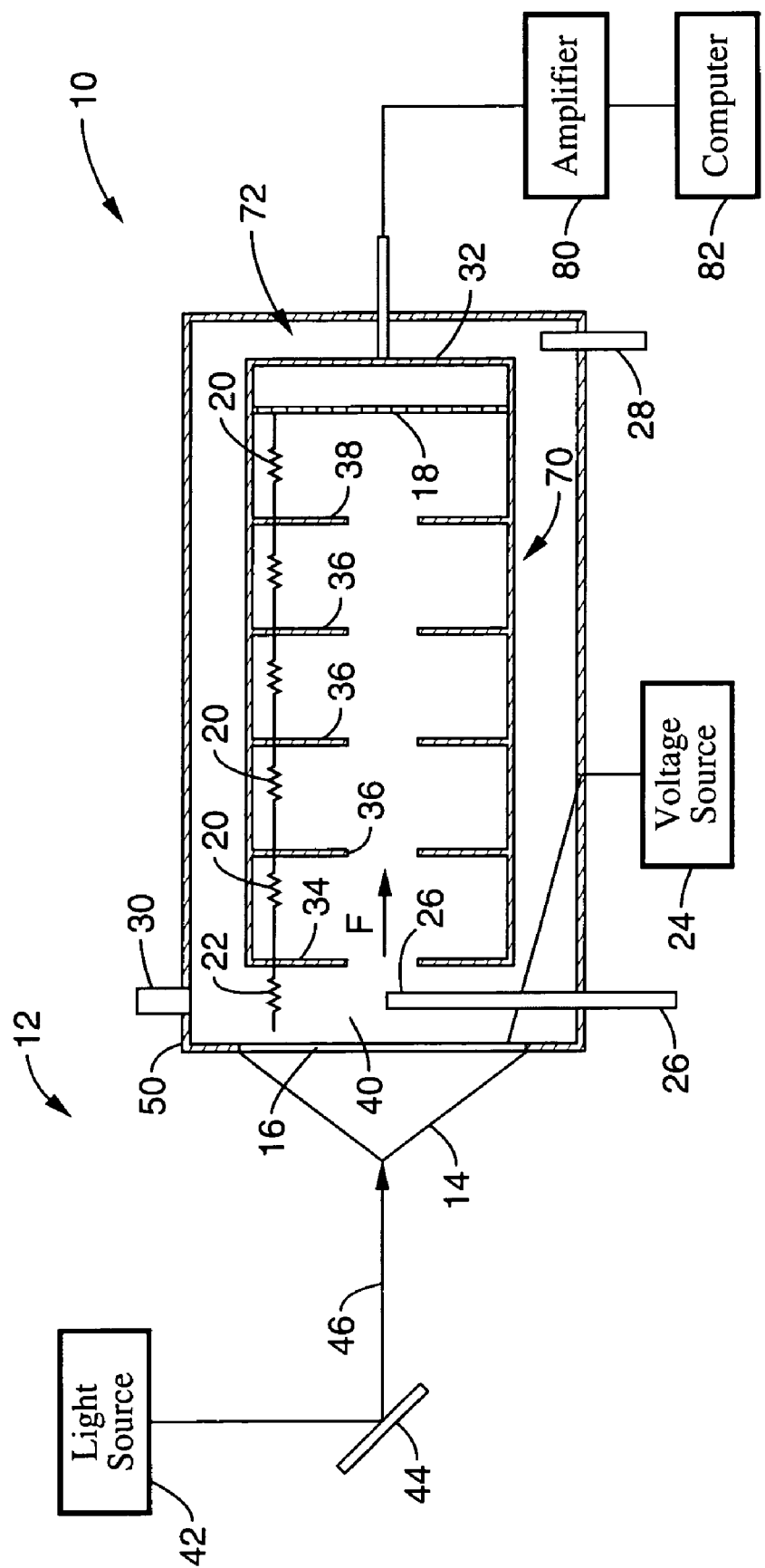
FIG. 1 is a schematic diagram of a photoemissive ion mobility spectrometer in accordance with the present invention.

FIG. 1 illustrates a schematic diagram of a photoemissive ion mobility spectrometer 10 in accordance with the present invention. The IMS system is comprised of three main parts: (1) a photoemissive ionization source 12 for generation of free electrons; (2) a drift tube 70, for separation of ions; and (3) a detector 72 for detection of ions.

The photoemissive source 12 generally comprises a light source 42 that is configured to direct a beam of light 46 at optical element 14. The backside of optical element 14 has a metal coating or plating 16, which is positioned at the opening of the ionization chamber 40. The impinging light beam 46 on the thin film generates an electron photoemission of free, low-energy electrons.

Coating 16 preferably comprises a thin-film gold plating, but may also comprise other thin conducting films such as silver or aluminum. Thin films may also be varied or added to lower the effective work function of the film surface.

The photoemissive source 12 and optical element 14 are configured to direct light beam 46 to impinge on metal coating 16 such that the light beam undergoes total internal reflection (i.e. all, of the UV light is reflected off of the metal coating). As a result, no UV light is transmitted into the ionization chamber 40, avoiding photochemistry of the analytes.

Figure 2:
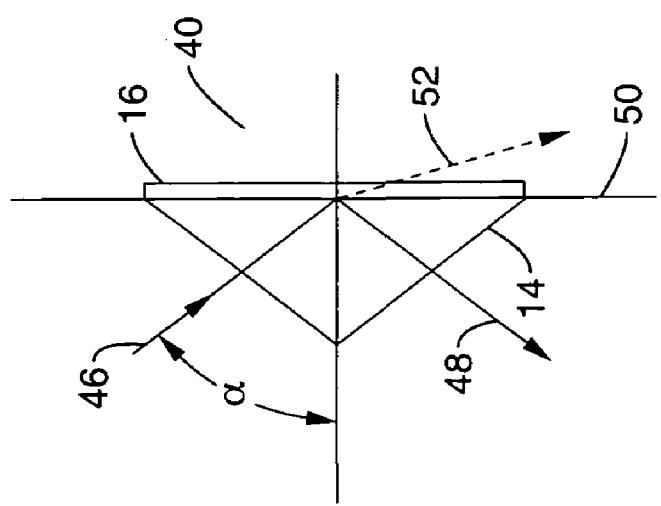
FIG. 2 is a detailed view of an exemplary ionization source utilizing total internal reflection in accordance with the present invention.

As shown in FIG. 2, the optical element 14 may comprise a prism having its back side coated with thin film 16. The incoming beam 46 is directed at the prism toward the back surface having the thin film 16 at an angle of incidence $\alpha$. At smaller values of $\alpha$, the incoming beam 46 strikes the back surface and emerges from the optical element as a refracted ray 52 and reflected ray 48. However, as the angle $\alpha$ increases, the ray 52 refracts at a larger angle relative to the surface normal until it becomes parallel with the back surface, also known as the critical angle $\alpha_c$. For any angle of incidence $\alpha$ greater than the critical angle $\alpha_c$, light beam 46 will undergo total internal reflection (TIR), resulting in only a reflected beam 48, wherein none of the beam is refracted through the thin film 16 into the ionization chamber 40. Thus, the light source 42 and/or intermediary optics 44 of the present invention are positioned and oriented such that light beam 46 is directed at the thin-film surface 16 at an angle of incidence greater than the critical angle $\alpha_c$.

Optical element 14 may be any device capable of manipulating light beam 46 to impinge on thin film 16 under total internal reflection. For example, optical element 14 may comprise the bare core of ultraviolet fiber optics or waveguides having a thin film metal coating. The waveguide would generate a multitude of total internal reflections. Such evanescent waves would enhance photoemission and would be particularly useful in miniaturizing the device.

Figure 3:
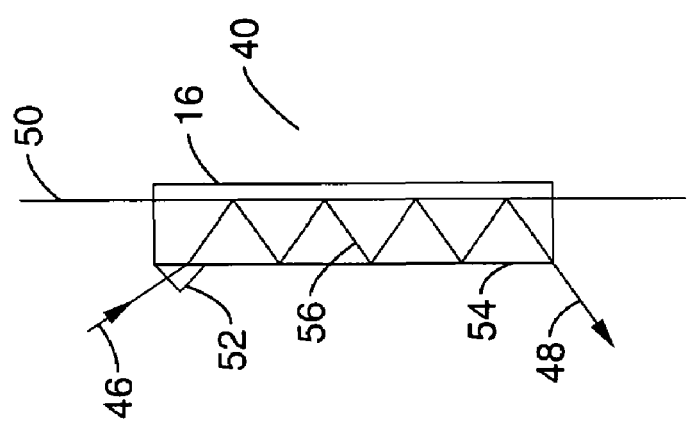
FIG. 3 shows a schematic diagram of an alternative ionization source with multiple internal reflections.

Photoemissive efficiency may also be increased with the use of multiple reflective TIR optical elements, as illustrated in FIG. 3. In this embodiment, light beam enters a transparent plate 54 via prism 52. The light propagates in a single-pass down the length of the plate by means of multiple internal reflections 56 from opposing plane-parallel surfaces, and then emerges out the end of the plate 54 as beam 48. The evanescent waves due to the multiple reflections enhance the photoemission of the device. Alternatively, by closing off the exit, the light beam may pass back through (i.e. double pass) the length of plate 54 to exit back out the entrance of the plate (e.g. at prism 52). In either case, the light is directed at a value above the critical angle $\alpha_c$ such that it impinges on the thin film 16 under total internal reflection.

Light source 42 may comprise any light source that is capable of producing photon energy that exceeds the effective work function of the thin film surface 16, or multiphoton processes that exceed the work function. Preferably, the light source is configured to emit light in the ultraviolet (UV) frequency range, as shorter wavelengths are generally more effective at generating free electrons, and are thus more efficient. An exemplary light source 42 may comprise a Nd:YAG laser, mercury or pulsed xenon lamp or the like. This could include the harmonics of microchip lasers or fiber optic lasers, flash lamps, and in particular ultraviolet light emitting diodes (LED's).

Figure 4:
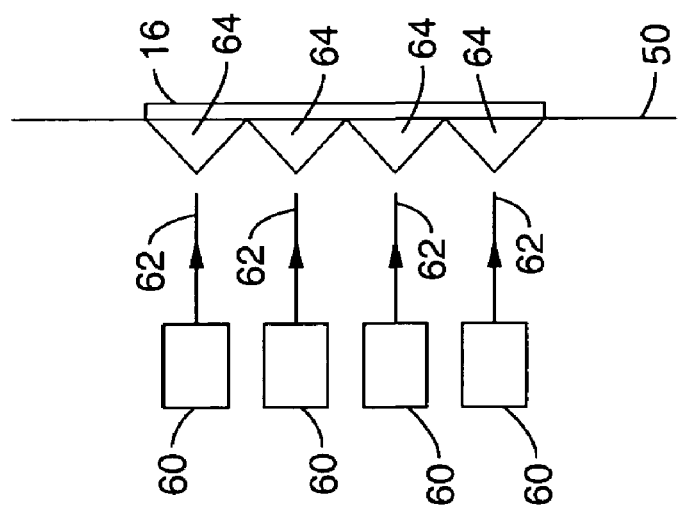
FIG. 4 illustrates a photoemissive source using a plurality of UV LED's in accordance with the present invention.

For example, FIG. 4 illustrates a configuration using an array of LEDs 60 placed around the circumference of the photoemitter or thin film 16, such that a plurality of UV light beams are directed to an array of individual optical elements 64.

Referring back to FIG. 1, the ionization chamber 40 is defined by outer walls 50 that enclose the opening or window of the ionization source (i.e. optical element 14 and thin film 16). A drift tube 70 is positioned in line with the ionization source in the chamber 40, and generates an electric field to facilitate movement of ions from the thin film to the detector 72 located at the end of the drift tube 70. It is appreciated that the drift tube 70 may also be integral with, or comprise the outer wall 50.

When the ions are then subjected to the electric field generated in the drift tube, they are accelerated towards the detector 72. The ions get separated by their mobility (depending on their mass, size, and shape), and arrive at the detector plate 32 in order from the fastest to the slowest, generating a response signal characteristic for the chemical composition of the measured sample.

The drift tube 70 generally comprises a plurality of guard rings, including first ring 34, intermediate rings 36 and last ring 38, equally spaced and concentrically positioned along the drift tube 70. The embodiment shown in FIG. 1 illustrates three intermediate rings 36 (for a total of five guard rings). However, it is appreciated that any number of rings may be used. For example, the number of rings may be increased. In addition, a continuous high resistivity coating could be used on the inside surface of the an insulating drift tube.

The first ring 34 is coupled to the thin film 16 via a resistor 22, and subsequent rings are separated by additional resistors 20. A high voltage source 24 is coupled to the drift tube 70 and corresponding resistors. The far end of the drift tube is capped by an aperture grid 18 and Faraday collector 32 of detector 72. Signals from the collector 32 are then amplified by amplifier module 80, which may include a pre-amplifier, and then analyzed with a computer 82.

For use in detecting the composition of sample surfaces, adsorbed explosive molecules from a sample surface are directly injected into the spectrometer 10 through a heated inlet 26. The characteristics of the photoemissive ionization approach allows the use of air as the carrier gas with direct vaporization of adsorbed explosive molecules from surfaces, which are then injected into the photoemissive ion mobility spectrometer through inlet 26 via a fan, pump, pressurized source (not shown) or other fluid flow means. The operating temperature of the device may be varied to optimize the flow of gasses and mixing in the ionization chamber 40 and thereby optimize oxygen based transfer of charge to the analytes.

A drift gas inlet 28 provides supply and flow of counter-flowing drift gas, such as nitrogen or air into the chamber 40. The positioning of the drift gas inlet at the rear of the chamber 40, along with the exhaust gas outlet 30 near the ionization source, maintains a counter-flow in the drift region to limit analyte vapor to the space immediately surrounding the photoemitting gold film 16 (i.e. the counter-flowing drift gas prevents neutral molecules from entering the drift region).

In addition to the setup embodied above, the photoemissive ionization source 12 may also be coupled with alternative drift configurations, such as the high field asymmetric ion mobility spectrometer shown in Krylov, E., et al., *Journal of Physical Chemistry* 2002, 106, 5437-44, incorporated herein by reference in its entirety.

Experiment

A test setup was constructed using an experimental apparatus similar to the schematic diagram of the spectrometer shown in FIG. 1. The photoemissive source was a 12.7 mm fused-silica equilateral prism 14 (ESCO Products, Inc., Oak Ridge, N.J.) with a 20 nm gold coating 16. The drift tube 70 consisted of five rings from a Chemical Agent Monitor (CAM) IMS followed by a gold plated aperture grid 18 (Graseby Dynamics, Ltd. Wafford, UK) in front of a copper collector Faraday plate 32. The separation between the thin gold film 16 and the first guard ring 34 of the drift tube was 4.5 mm with a 350 k$\Omega$ resistor between them. The separation between the drift-tube rings 36 and between the last ring 38 and the grid 18 was approximately 7.2 mm. The aperture grid was separated in a ceramic mount by 0.8 mm from the 2-cm diameter copper collector with a 400 k$\Omega$ resistor between them. A voltage divider consisting of a chain of 300-k$\Omega$ resistors provided the potentials for the drift guard rings to generate a uniform electric field along the axis of the drift tube 70.

A bias of 2000 V was selected and maintained between the repeller and collector producing an electric field of 708 V/cm between the gold film 16 and the first guard ring 34 and an average drift region electric field of 369 V/cm in the drift tube for all measurements reported below. An electric field of approximately 4425 V/cm was maintained between the grid and collector. The PE-IMS was operated at room temperature and atmospheric pressure.

Two different configurations were used to transport sample gases into the PE-IMS system. In detecting trichloroethylene (TCE) or methylene chloride in air or nitrogen, a gas mixture was prepared by injecting the neat analyte or analyte mixed in the non-electronegative solvent cyclohexane into a sealed 5-L, round-bottomed glass flask (not shown) through a septum with a 50 μL or 10 μL syringe. A stainless steel tube delivered carrier gas (nitrogen or air) to the bottom of the flask while a shorter tube extracted mixed gas from the center of the flask and it was delivered to the ionization region of the PE-IMS through a room temperature teflon tube 26.

To deliver vapors of nitroaromatic compounds, solids of very low vapor pressure at room temperature and ambient pressure, a 0.25-inch Swagelok tee (not shown) was placed in the gas delivery line. Several granules of the analyte solid sample (p-nitrotoluene; 2,4-dinitrotoluene; or 2,6-dinitrotoluene) were placed in the Swagelok cap attached to the bottom of the tee. The cap was lowered into a beaker containing softly boiling water to melt the solid and increase its vapor pressure. The room temperature carrier gas, e.g. ultra pure nitrogen gas or breathing-grade compressed air, was flowed through the tee, carrying the gas-phase analyte molecules to the ionization region of the PE-IMS through a room temperature teflon tube 26. Counterflowing nitrogen, 900 mL/min, was maintained in the drift region to limit analyte vapor to the space immediately surrounding the photoemitting gold film 16.

The fourth harmonic of a Continuum Nd:YAG Surelite II laser (at 266 nm) was used as light source 42 to deliver UV light onto the thin gold film 16. The laser was operated at 10 Hz repetition rate delivering pulses of approximately 5-ns temporal width. The pulse energy was attenuated to about 230 µJ. Pulse energy data were acquired using a Molectron pyroelectric detector (J9LP-1) at the beginning of the experiment.

In all configurations, the current induced by the movement of ions in the volume between the aperture grid 18 and the collecting electrode 32 was amplified $10^8$ V·A$^{-1}$ by a pre-amplifier (80) and then fed into a Tektronix TDS 540 or 620A digital storage oscilloscope (not shown). A FEMTO Messtechnik GmbH model HCA-10M-100k-C high speed current amplifier (80) with $10^5$ V/A amplification was substituted for the pre-amplifier to detect the free electron waveforms. A program written in C++ controlled data acquisition, downloaded binary waveforms from the digital storage oscilloscope through a GPIB card, translated binary data to ASCII data, and then saved the data as files in the controlling computer 82. Acquisition averaging of at least 20 and as many as 125 laser shots with a record length of 500 sample points was used.

The chemicals used in the experiment were 2,4-dinitrotoluene (2,4-DNT); 2,6-dinitrotoluene (2,6-DNT); and p-nitrotoluene (p-MNT). Solvents used were methylene chloride, photometric grade TCE, and spectrophotometric grade cyclohexane. One microliter neat liquid TCE or methylene chloride was diluted with 1 mL HPLC grade non-electronegative cyclohexane solvent.

With the configuration of the present invention, the shutter grid at the entrance of the drift tube with its significant ion losses and its associated gating electronics were eliminated. The ultraviolet light generates thermal electrons, e$^-$, by the photoelectric effect. Since the electrons are generated as a pulse, the entrance grid shutter is not needed. In air, the thermal electrons have a lifetime of $2\times10^{-8}$ s, corresponding to traveling only ca. $1.2\times10^{-2}$ cm, before conversion to an $O^{2-}$ reactant ion (Begley et al., *Journal of Chromatography* 1991, 588, 239-49).

The target compound M is ionized by the following system of reactions:

(1)

(2)

(3)

This corresponds to a half peak width of 20 µs in the reactant ion peak due to the electron drift in air. With air as carrier gas, the photoemissive electron IMS of the present invention performs comparable to a conventional radioactive $^{63}$Ni emitter IMS.

Experiment Results

Using the spectrometer of FIG. 1, electrons were effectively generated by photoemission in flowing atmospheric pressure nitrogen. Since molecular nitrogen does not capture low-energy electrons, the pulse of electrons produced from the photoemissive source remains intact while passing through nitrogen to the collector plate, giving rise to a very large, abrupt peak in the ion mobility spectrum. Because the drift velocity of electrons in nitrogen is about $3.8\times10^5$ cm·sec$^{-1}$, or around two orders of magnitude faster than most other negative ions, the electron signal appears promptly in the ion mobility spectrum.

Figure 5:
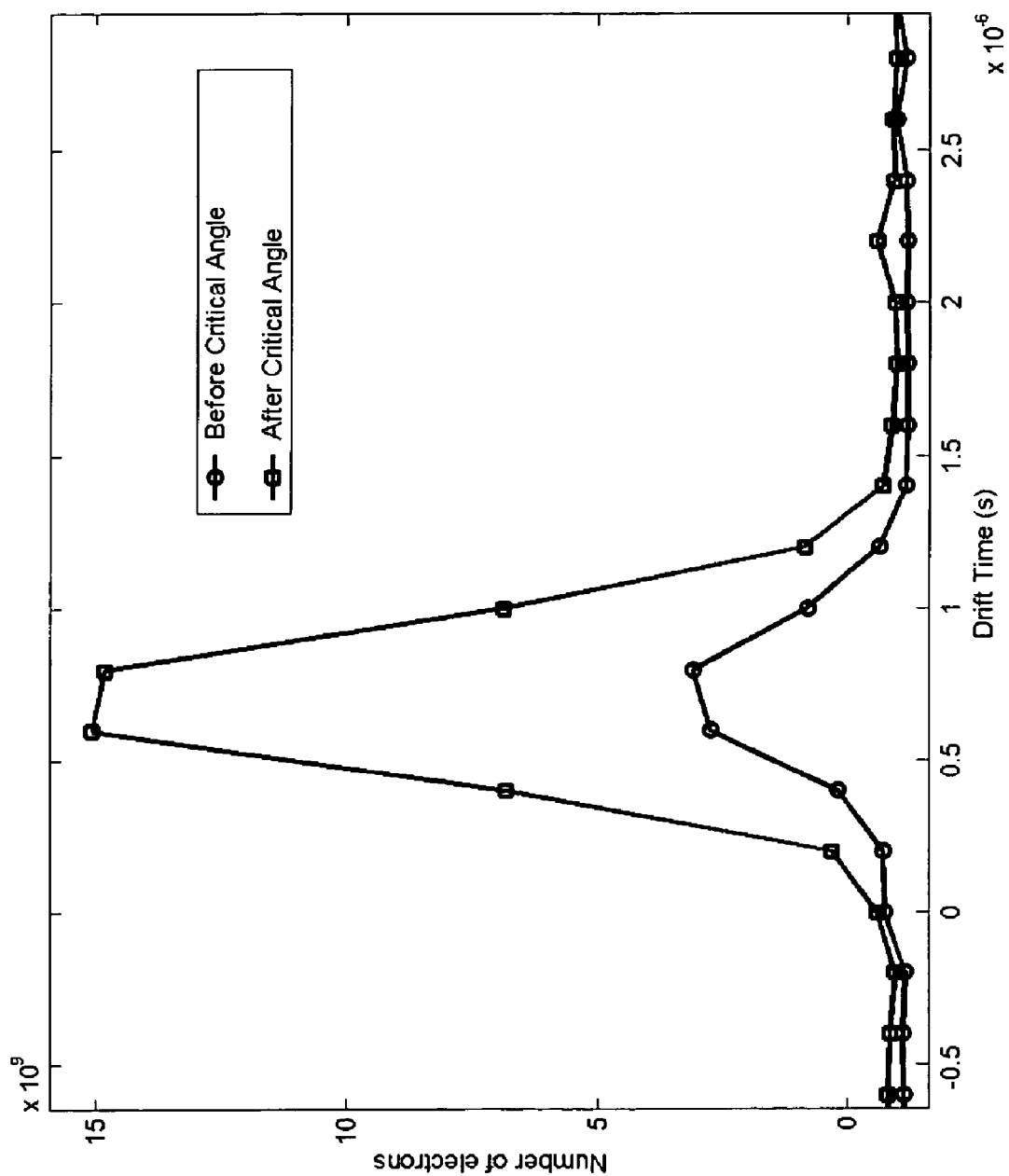
FIG. 5 shows test results of the negative ion mobility spectrum of free electrons in nitrogen at incident angles above and below the critical angle.

This effect is illustrated in FIG. 5. Also illustrated in FIG. 5 is a significant enhancement (>500% increase) in the photoemission yield achieved by the photoemissive source 12 of the present invention when the angle of incidence on the back side of the gold coating 16 is increased beyond the critical angle. Peak electron currents of 2.5 nanoamp were easily achieved, and higher currents can be achieved with optimization. Whereas the linear range of the conventional IMS is limited by the total ion current of the $^{63}$Ni radioactive source, the ability of the present invention to easily vary the electron ion current will extend the linear operating range of the IMS.

Introduction of an electron-attaching species, such as a chlorinated hydrocarbon, decreases the charge collected in the free electron peak due to electron capture, as expected. The concentration analyte in the carrier gas (ultra pure nitrogen gas) slowly decreases by exponential dilution with time given by:

$$C = C_0 e^{-\alpha t} \qquad (4)$$

$$\alpha = \frac{Q}{V}$$

where C is the analyte concentration in the exiting gas, $C_0$ is the initial analyte concentration, V is the volume of the flask (not shown), Q is the constant flow rate of gas through the chamber 26, and t is the duration of the gas flow.

Figure 6:
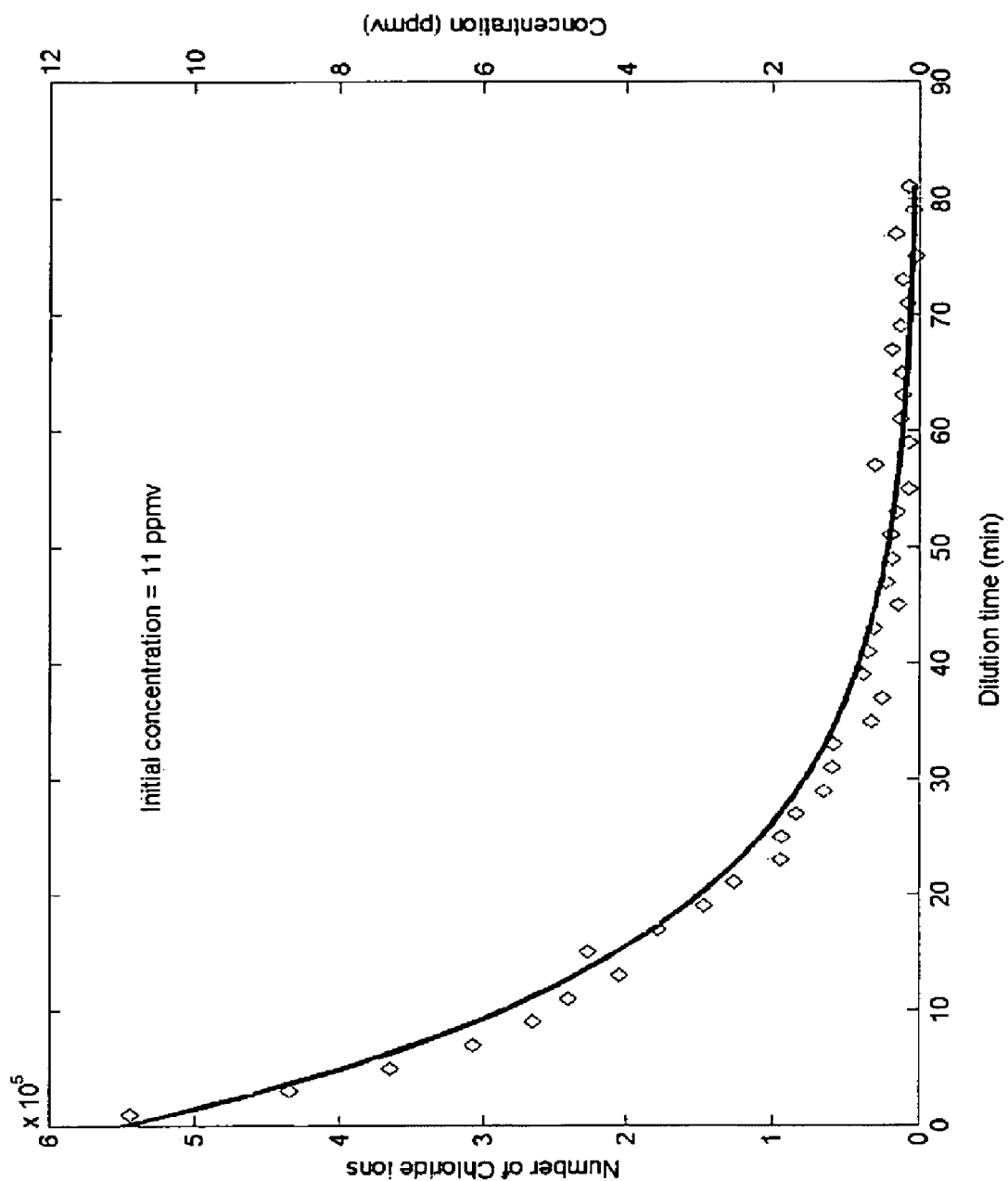
FIG. 6 shows the chloride ions collected during exponential dilution of a 5 L mixture of 11 ppmv TCE at a dilution flow rate of 28 mL/min nitrogen.
Figure 7:
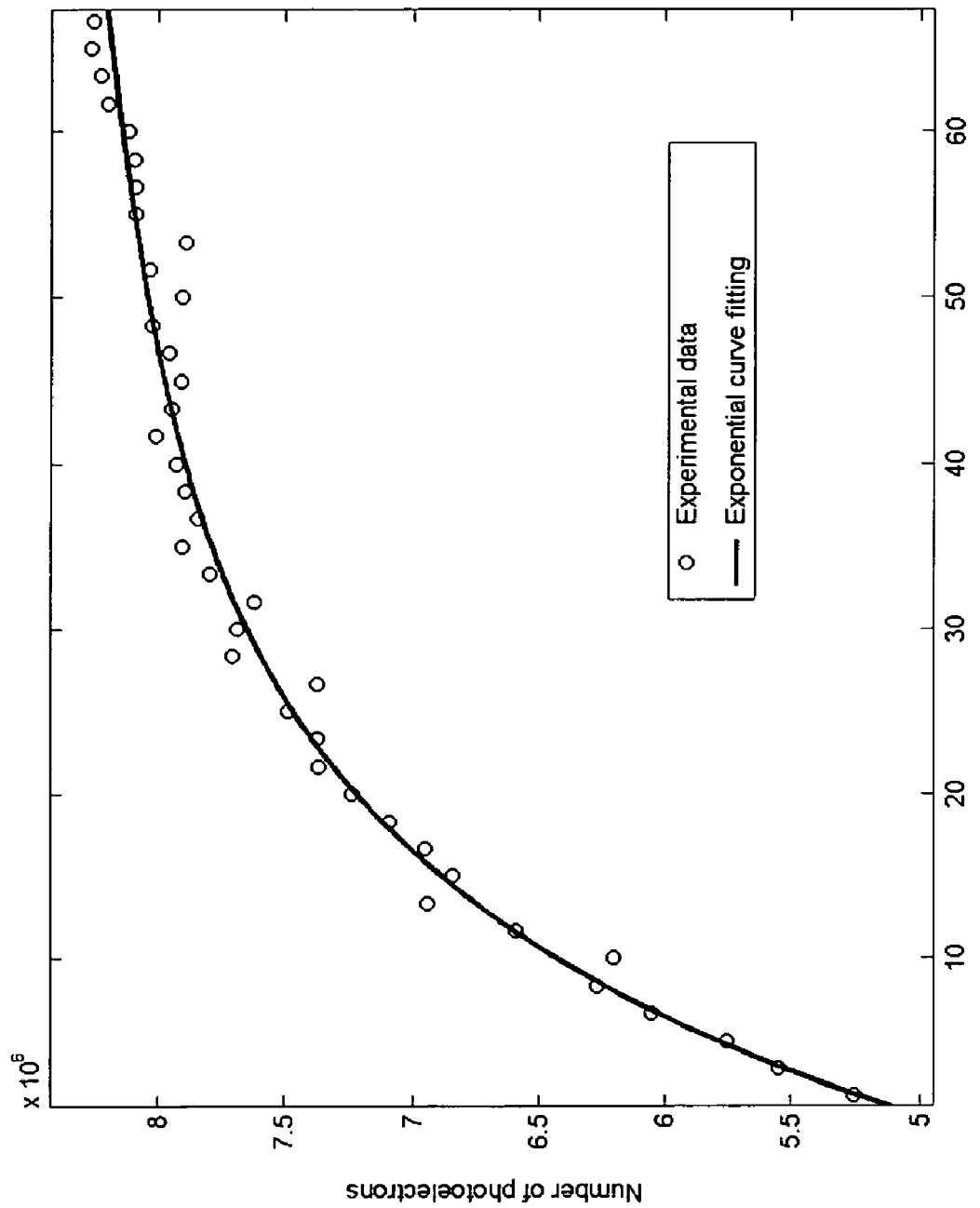
FIG. 7 shows free electrons collected during exponential dilution of a 5 L mixture of 11 ppmv TCE at a dilution flow rate of 28 mL/min nitrogen.

FIG. 6 shows the exponential decay in the number of chloride ions detected for TCE in ultra pure nitrogen with the carrier gas flowing through the flask at the rate of 28 mL/min for a period of about 1.5 hours. The corresponding exponential increase in the free electrons reaching the collector is presented in FIG. 7. Because different pre-amplifiers were used, the data were acquired in similar but separate acquisitions.

Figure 8:
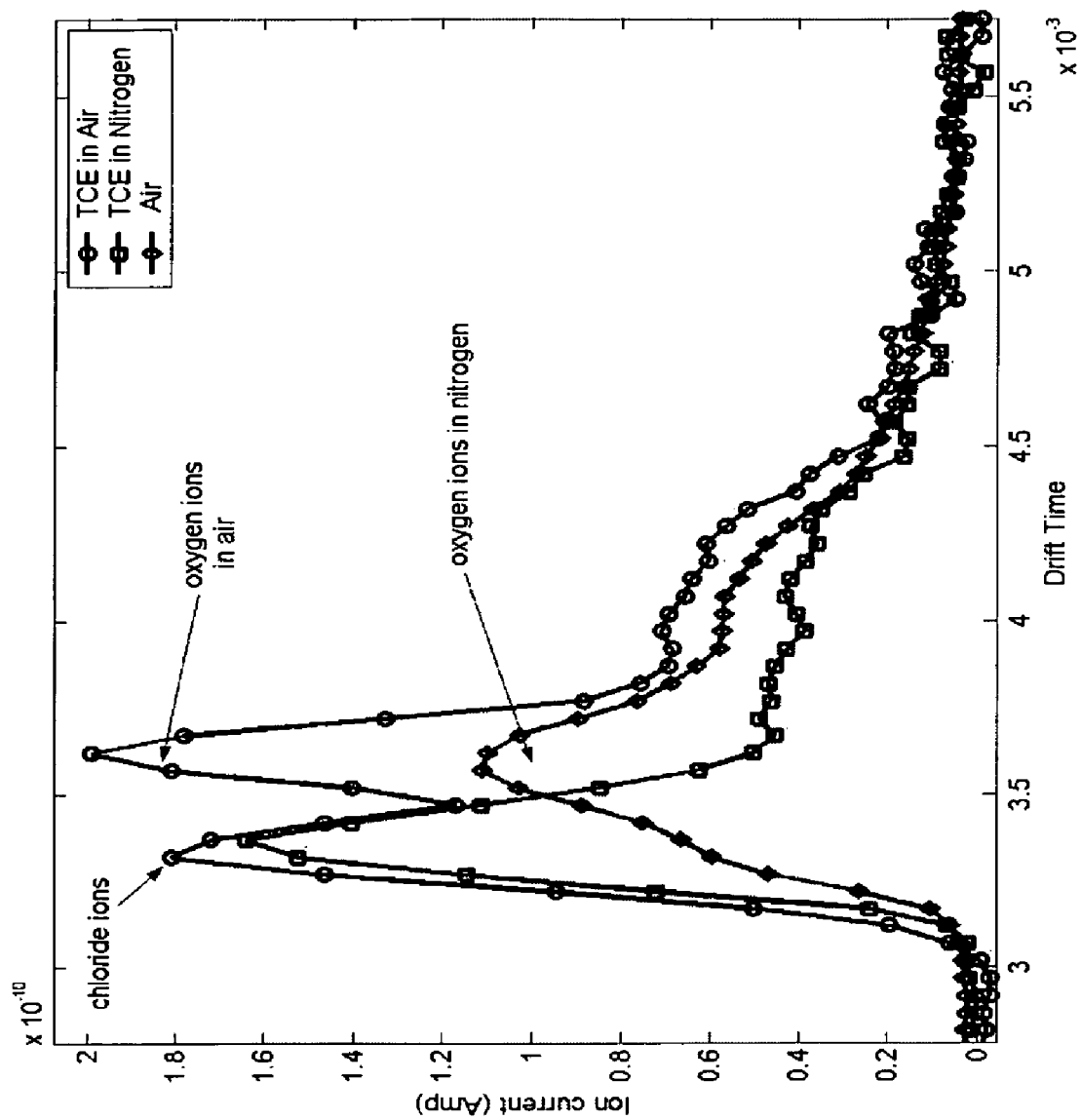
FIG. 8 shows the ion mobility spectra of chloride and oxygen ions generated from 11 ppmv TCE in nitrogen and air.

Since the ECD strongly responds to vapors of chlorinated species, such as methylene chloride and TCE, that release chloride ions upon attachment of low-energy free electrons, measurements were made to detect TCE and methylene chloride at room temperature and ambient pressure in air. FIG. 8 shows the ion mobility spectra of 11 ppmv TCE in air compared with the same amount of TCE in ultra pure nitrogen. The electron capture events occur near the photoemitter. The low-energy electron attachment cross-section of oxygen is much smaller than that of most chlorocarbons. However, the concentration of oxygen (21%) in air is much higher than that of the trace chlorinated (low ppmv). Therefore, oxygen will initially capture a significant portion of the emitted photoelectrons, but because oxygen only reversibly binds low-energy electrons via a non-dissociative electron attachment process (i.e. the oxygen molecule is not destroyed upon attachment of an electron), electrons eventually attach irreversibly to the more electronegative chlorocarbon molecules. Chlorinated compounds are also known to react quickly with $O_2^-$ in the gas phase to yield chloride ions by dissociative electron attachment. Due to their higher electronegativity, the chlorocarbons are the terminal electron capturing species regardless of whether or not they directly capture the emitted electrons.

Reduced ion mobility values, $K_0$, were calculated using the following equation:

$$K_0 = \frac{v}{E} \times \left(\frac{p}{760}\right) \times \left(\frac{273}{T}\right) = \frac{L}{E \times t} \times \left(\frac{p}{760}\right) + \left(\frac{273}{T}\right) \quad (5)$$

where L is the length of the drift tube 70 (3.59 cm), E is the magnitude of the drift field (372.4 V/cm), t is the drift time, v is the drift velocity, $K_o$ is reduced ion mobility in $cm^2 \cdot v^{-1} \cdot s^{-1}$, p is atmospheric pressure (750 torr), and T is the temperature of the drift tube (298 K). The length, L, was measured from the first electrode (e.g. ring 34) of the drift tube 70 to the collector 32. Reduced ion mobilities ($K_0$) of 2.45 $cm^2$ $V^{-1}$ $s^{-1}$ and 2.64 $cm^2$ $V^{-1}$ $s^{-1}$ were determined for the oxygen ion peak and chloride ion peak from the TCE and methylene chloride measurements. These two values are lower than published values of 2.5 $cm^2$ $V^{-1}$ $s^{-1}$ (oxygen ions) and 2.94 $cm^2$ $V^{-1}$ $s^{-1}$ for the mobilities of molecular oxygen and chloride anions in air, but are reasonable considering the strong possibility of extensive clustering of oxygen and chloride anions in the drift volume, resulting in the decrease of reduced ion mobilities of oxygen as well as chloride ions.

In addition, FIG. 8 illustrates that the chloride and oxygen ion signals contain Gaussian peak deformations. These deformations may be related to clustering of ions with water molecules.

Figure 9:
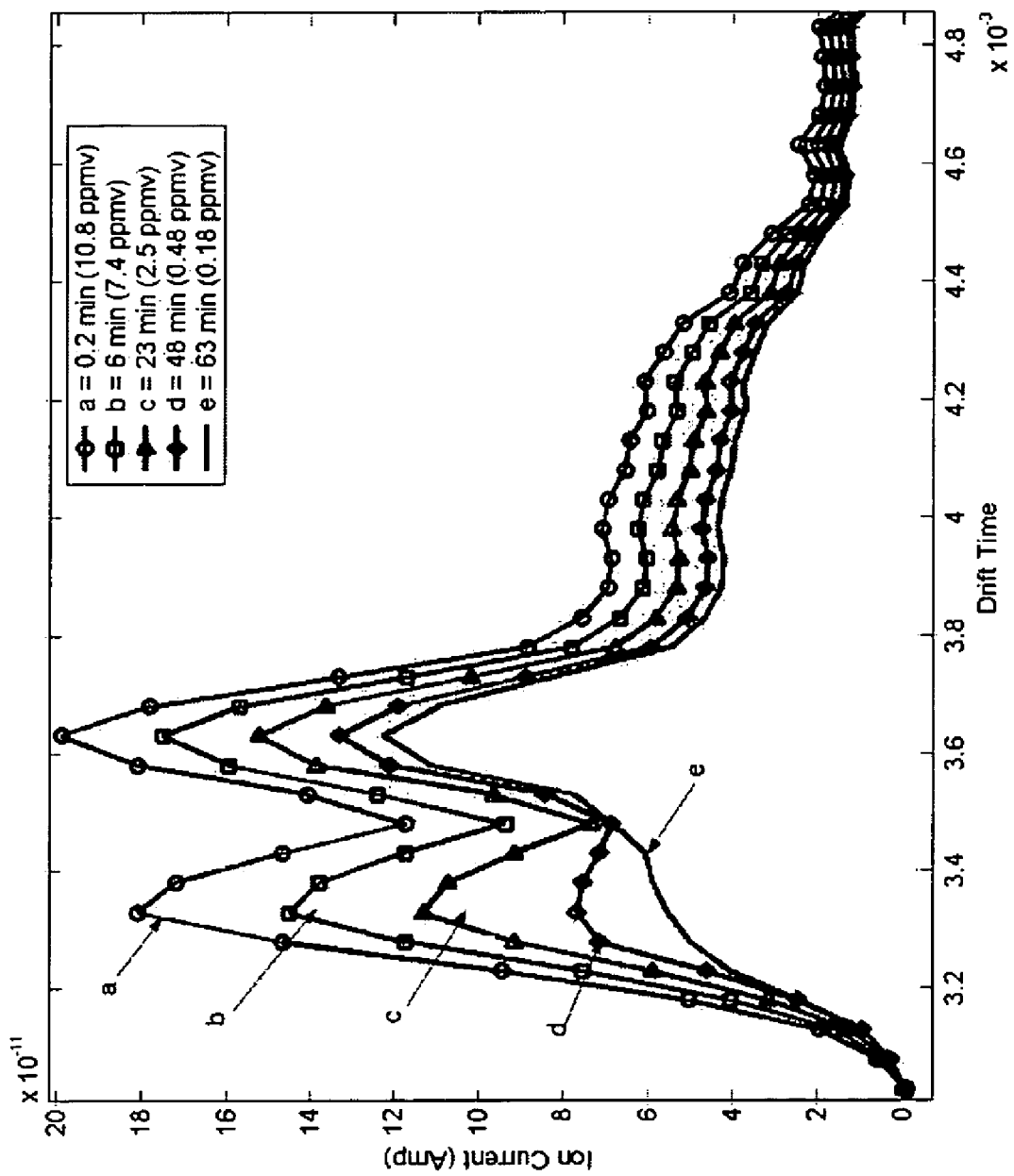
FIG. 9 shows the chloride ion current due to low-energy electron attachment to TCE as a function of drift time at ambient pressure in air.

FIG. 9 shows how the ion mobility spectra of TCE changes with dilution time at room temperature in air. Similar results were produced for methylene chloride but with poorer sensitivity.

Figure 10:
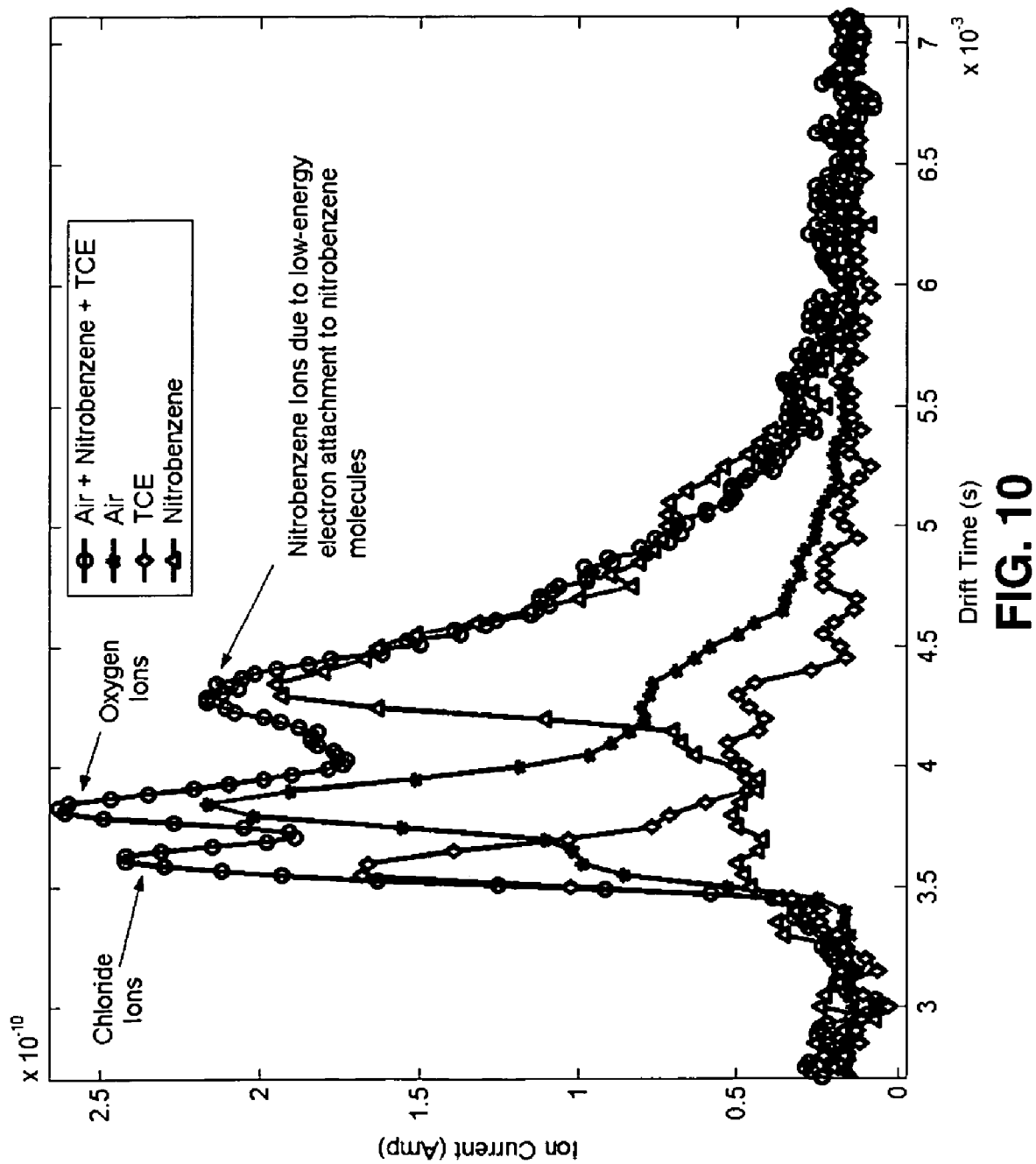
FIG. 10 shows the ion mobility spectra of 3.8 ppmv TCE and 15 ppmv nitrobenzene in nitrogen and breathing-grade air.

The negative ion mobility spectra obtained for a mixture of 3.8 ppmv TCE and 15 ppmv nitrobenzene in breathing-grade air are displayed in FIG. 10. The collected chloride ions and nitrobenzene ions are well separated from the oxygen ions. Three ion mobility peaks are observed with reduced mobilities of 2.40 $cm^2 \cdot V^{-1} \cdot s^{-1}$, 2.60 $cm^2 \cdot V^{-1} \cdot s^{-1}$, and 1.85 $cm^2 \cdot V^{-1} \cdot s^{-1}$ obtained using equation (5). These reduced ion mobilities are lower than but comparable to published values for ion mobilities of bare molecular oxygen (2.5 $cm^2 \cdot V^{-1} \cdot s^{-1}$), chloride (2.94 $cm^2 \cdot V^{-1} \cdot s^{-1}$), and nitrobenzene (1.74 $cm^2 \cdot V^{-1} \cdot s^{-1}$) (1.86 $cm^2 \cdot V^{-1} \cdot s^{-1}$) anions. The lower values are likely due to extensive clustering of anions in the drift volume and measurement error (or measurement precision). Experimental results have shown that, in the IMS spectrum of nitromethane, two peaks were observed. While, in the case of nitrobenzene, only the parent negative ion was observed at atmospheric pressure and 310 K, in agreement with the present results in FIG. 10.

Since the vapor pressure of nitrobenzene liquid is very low, the nitrobenzene gas-phase molecules stick to the wall of the 5 L flask, the inside surface of the cell housing the drift tube 70, and the teflon tubing 26. Therefore, even though the initial concentration of nitrobenzene in the 5 L flask full of breathing-grade air is known, the nitrobenzene vapor concentration reaching the PE-IMS is unknown.

In the presence of a nitrogen carrier gas, the reactant ions are low-energy electrons while the reactant ions are negative oxygen ions with a carrier gas of breathing-grade air. If breathing-grade air is used as a carrier gas, low-energy electrons emitted by the thin gold film 16 attach to abundant oxygen molecules to form negative oxygen ions called reactant ions. The oxygen anions collide with the TCE or methylene chloride molecules, resulting in chloride anions. The production of chloride anions is confirmed by the fact that the position of the chloride ion peak in ultra pure nitrogen is the same as that of the chloride ion peak in air.

The separation of ion mobility spectra was very sensitive to the position of the end of the teflon carrier gas tube 26 placed in the space between the photoemitter and the first guard ring 34 of the drift tube 70. The mixing of the high flow rate nitrogen drift gas (900 mL/min) and the carrier gas (28 mL/min) did not produce the desired layer of oxygen molecules to capture all of the emitted electrons. A large number of electrons emitted by the gold film 16 were collected unattached to either oxygen molecules or other molecules of interest indicating that only a small amount of oxygen molecules in air captured electrons to form oxygen ions for the configuration that gave the best separation of ion peaks. To provide a flow of reactant gas for the capture of all the free electrons in a short distance, a curtain flow gas of air (as shown in Tabrizchi, Mahmoud; Abedi, Azra *International Journal of Mass Spectrometry* 2002, 218, 75-85, incorporated herein by reference) or other reactant gas such as methylene chloride (for nonchlorinated detection) may be introduced before the carrier gas flow. Attenuation of the ultraviolet light may also be employed to reduce the oxygen peak for separation from the chloride peak.

Nitro-organic explosives have relatively high electronegativities and, thus, favor the formation of stable, negative gas-phase ions via atmospheric pressure chemical ionization reactions. Previous studies suggested that the ionization of nitro-organic explosive compounds in an electron capture detector IMS depended on the carrier gas composition. Investigation of the ion-molecule chemistry for the negative ionization of nitroaromatic compounds, such as mono-nitrotoluenes; 2,4-DNT; and 2,6-TNT, in air as well as in nitrogen, revealed that the dominant ions created with nitrogen as a carrier gas were $M^-$ via electron attachment at 166° C. at atmospheric pressure. However, the main ions generated in air carrier gas, with $O_2^-$ as a reactant ion produced from electron attachment to oxygen molecules, were $(M-H)^-$ resulting from proton abstraction for every nitroaromatic compound of interest except m-MNT, which remained as $M^-$, as shown in Eqs. 6 and 7.

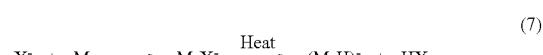

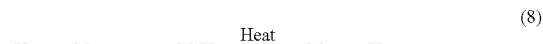

where $e^-$ is an electron in nitrogen and $X^-$ is $O_2^-$ or $Cl^-$ with an acidic proton in air.

Equation 6 represents the reaction between reactant ions, free electrons, and sample molecules in nitrogen (associative electron attachment), and Eq. 7 denotes the reaction in air. Previous experimental data indicated that the proportion between $M^-$ and $(M-OH)^-$ was quantitatively controlled by the amount of $O_2$ in nitrogen which worked as a carrier gas.

In summary, atmospheric pressure reactions of nitrotoluene compounds with IMS methods produce $M^-$ ions when only thermal electrons are present by using nitrogen as a carrier gas, to which photoemitted electrons do not attach. In the presence of $O_2^-$ ions resulting from free electron attachment to oxygen molecules, proton abstraction occurs to yield $(M-H)^-$.

The negative ion mobility spectra recorded for 2,4-DNT; 2,6-DNT; and p-MNT are displayed in FIGS. 11-13. They were taken in the presence of either nitrogen or air carrier gas and nitrogen drift gas at atmospheric pressure and room temperature. Since the vapor pressures of 2,4-DNT; 2,6-DNT; and p-nitrotoluene are very low at room temperature, and thus absorb on the teflon tube and IMS surfaces, their concentrations in the IMS are unknown. Two characteristic ion mobility species were also observed in air while there was only a single peak in nitrogen for these species. The reduced ion mobility values presented in Table 1 were calculated in the presence of either air or nitrogen carrier gas and nitrogen drift gas at room temperature based on the IMS spectra using Eq. (5). The reduced ion mobilities measured for 2,4-DNT; 2,6-DNT; and p-MNT show satisfactory consistency with the literature values obtained at 50° C., 250° C., or 166° C. listed in Table 1. Moisture has been seen to alter drift times of ions by expanding hydration shells and making ions larger and mobilities lower. In FIGS. 11-13, it appears that the analyte ion signals contain back shoulders. The back shoulders are likely due to the clustering of analyte and oxygen ions with water molecules.

The nitro-organic signal was significantly enhanced by the presence of oxygen at room temperature, as seen in FIGS. 11-13. The fortuitous signal enhancement observed in the presence of air indicates that explosive residues may be effectively detected on surfaces by pulsed heating of the surface with subsequent direct injection of the vapor containing air into the PE-IMS through a heated inlet.

The PE-IMS of the present invention is capable of detection of a wide variety of electron-attaching vapors, including: nitro-containing explosives, chlorinated solvents, barbiturates, many pesticides, and several lachrymators. It has been demonstrated that using photoemissive ionization via backside illumination eliminates the need for a radioactive source and simplifies the required electronics.

More importantly, using total internal reflection of the ultraviolet light enhances the electron emission by a factor of at least five and prevents photochemistry of the analytes. The significantly shorter PE-IMS pulse duration, compared to that available in a commercially available IMS with a shutter grid, improves resolution. The IMS section of the instrument may also be upgraded to that of commercial grade instruments to improve resolution, sensitivity and false alarm rates for explosives better than conventional $^{63}$Ni ionization instruments due to the simplified chemistry. The fortuitous enhancement of the nitro-organic signal by oxygen in air also promotes the direct vaporization of explosive molecules from surfaces and intake into the photo-emissive ionization chamber through a heated inlet.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

PE-IMS of 2,4-DNT; 2,6-DNT; and p-MNT in nitrogen or air drift gas

| Compounds | Carrier/drift gas | Species | $K_0$ Literature ($cm^2/V\ s$) | T (° C.) | $K_0$ Measured ($cm^2/V\ s$) | T (° C.) |
|---|---|---|---|---|---|---|
| 2,4-DNT | $N_2/N_2$ | $M^-$ | 1.61 | 50 | 1.68 | 25 |
| 2,4-DNT | $Air/N_2$ | $(M - H^-)$ | 1.62 (1.67) | 250 (50) | 1.66 | 25 |
| 2,6-DNT | $N_2/N_2$ | $M^-$ | 1.52 | 50 | 1.58 | 25 |
| 2,6-DNT | $Air/N_2$ | $(M - H^-)$ | 1.61 | 50 | 1.65 | 25 |
| p-MNT | $N_2/N_2$ | $M^-$ | 1.79 | 250 | 1.84 | 25 |
| p-MNT | $Air/N_2$ | $(M - H^-)$ | 1.74 | 166 | 1.77 | 25 |

What is claimed is:

1. A photoemissive ion mobility spectrometer for the detection of an analyte, comprising:
   an ionization chamber configured to receive the analyte;
   a photoemissive ionization source disposed at a first end of the ionization chamber;
   the photoemissive ionization source comprising an optical element having a back surface;
   wherein the back surface of the optical element is disposed adjacent the ionization chamber;
   the optical element configured to receive a beam of light from a location external to the ionization chamber and direct the beam at the back surface;
   wherein back surface of optical element is configured to illuminate under total internal reflection of the beam such that the beam does not enter the ionization chamber;
   wherein the backside illumination of the optical element generates ions in the chamber; and
   wherein said ions are characteristic of the received analyte.

2. A spectrometer as recited in claim 1, further comprising:
   a detector disposed at a second end of the ionization chamber opposite the photoemissive ionization source;
   wherein the detector is configured to detect presence of said ions generated by the photoemissive ionization source.

3. A spectrometer as recited in claim 2, further comprising:
   a drift tube disposed between the photoemissive ionization source and the detector;
   said drift tube configured to generate an electric field to separate said ions and direct the ions from the photoemissive ionization source to the detector.

4. A spectrometer as recited in claim 1, wherein the back surface of the optical element comprises a thin metal coating.

5. A spectrometer as recited in claim 4, wherein the metal coating comprises gold.

6. A spectrometer as recited in claim 4, wherein said optical element comprises a prism that is configured to direct the beam at the metal coating at an angle of incidence beyond a critical angle of the prism.

7. A spectrometer as recited in claim 1, the optical element is configured to generate multiple internal reflections on the back surface of the optical element.

8. A spectrometer as recited in claim 1:
wherein the ionization source comprises an UV light source configured to direct the beam of light at the optical element.

9. A spectrometer as recited in claim 8, wherein the UV light source comprises a laser or flash lamp.

10. A spectrometer as recited in claim 8:
wherein the ionization source comprises a plurality of UV light sources, and
wherein each of the UV light sources are configured to direct a beam of light at one of a plurality of individual optical elements.

11. A spectrometer as recited in claim 10, wherein the plurality of individual optical elements comprises a plurality of LED's.

12. A spectrometer as recited in claim 1, further comprising:
an inlet tube coupled to the ionization chamber;
wherein the inlet tube is configured to direct the analyte under ambient air into the ionization chamber.

13. A spectrometer as recited in claim 12, wherein the inlet tube is heated to vaporize the analyte from a sample surface for collection.

14. A method for detecting an analyte, comprising:
directing a beam of light at an optical element having a coating at one end;
said beam of light configured to illuminate the coating to produce photoemission;
reflecting said beam of light off of said coating under total internal reflection;
generating ions as a result of said beam of light illuminating the coating; and
detecting the presence of said ions opposite said optical element.

15. A method as recited in claim 14, further comprising:
separating said ions along an axis of a drift tube;
said drift tube having a free end disposed adjacent said optical element; and
detecting the presence of said ions on a second end of said drift tube opposite said optical element.

16. A method as recited in claim 15, wherein:
the analyte is carried into the chamber via a carrier gas;
and wherein separating said ions comprises directing a counter-flowing drift gas through a plurality of rings and an aperture grid to generate a uniform electric field along an axis of said drift tube.

17. A method as recited in claim 16, wherein the plurality of rings are separated by resistors;
and wherein a voltage is supplied to the rings to generate the electric field.

18. A method as recited in claim 15, further comprising:
measuring the reduced ion mobility of the ions generated in the drift tube.

19. A method as recited in claim 15, wherein directing a light source at an optical element comprises directing a laser at a prism having a thin gold plating.

20. A method as recited in claim 19, wherein said prism is configured to increase an angle of incidence of the laser on a back side of said plating beyond a critical angle.

21. A method as recited in claim 16, wherein the carrier gas comprises ambient air.

22. A method as recited in claim 21, wherein the ambient air is heated prior to entering the drift tube.

23. A method as recited in claim 21, wherein adsorbed analytes from a sample surface are directly injected into the drift tube through a heated inlet.

24. A photoemissive ion mobility spectrometer for the detection of an analyte, comprising:
an ionization chamber configured to receive the analyte;
a photoemissive ionization source disposed at a first end of the ionization chamber;
the photoemissive ionization source comprising an optical element having a back surface;
wherein the back surface of the optical element is disposed adjacent the ionization chamber such that it forms at least a portion of an internal wall of the ionization chamber;
the optical element configured to receive a beam of light from a location external to the ionization chamber and direct the beam at the back surface;
wherein back surface of optical element is configured to illuminate under total internal reflection of the beam such that the beam reflects external the ionization chamber;
a detector disposed at a second end of the ionization chamber opposite the photoemissive ionization source; and
a drift tube disposed between the photoemissive ionization source and the detector;
wherein the backside illumination of the optical element generates ions in the chamber, said ions being characteristic of the received analyte;
wherein said drift tube is configured to generate an electric field to separate said ions and direct the ions from the photoemissive ionization source to the detector;
wherein the detector is configured to detect presence of said ions generated by the photoemissive ionization source.

25. A spectrometer as recited in claim 24, wherein the back surface of the optical element is configured such that none of the beam enters the ionization chamber.

26. A spectrometer as recited in claim 24:
wherein the back surface of the optical element comprises a prism having a thin metal coating facing the ionization chamber;
wherein the prism is configured to direct the beam at the metal coating at an angle of incidence beyond a critical angle of the prism.

27. A spectrometer as recited in claim 24, the optical element is configured to generate multiple internal reflections on the back surface of the optical element.

28. A spectrometer as recited in claim 24:
wherein the ionization source comprises an UV light source configured to direct the beam of light at the optical element.

29. A spectrometer as recited in claim 24:
wherein the ionization source comprises a plurality of a plurality of UV light sources, and
wherein each of the UV light sources are configured to direct a beam of light at one of a plurality of individual optical elements.

30. A spectrometer as recited in claim 28, wherein the plurality of individual optical elements comprises a plurality of LED's.

31. A spectrometer as recited in claim 24, further comprising:
an inlet tube coupled to the ionization chamber;
wherein the inlet tube is configured to direct the analyte under ambient air into the ionization chamber.

32. A spectrometer as recited in claim 30, wherein the inlet tube is heated to vaporize the analyte from a sample surface for collection.

* * * * *